US007259003B2

(12) United States Patent
Livshits et al.

(10) Patent No.: US 7,259,003 B2
(45) Date of Patent: Aug. 21, 2007

(54) *ESCHERICHIA* BACTERIA TRANSFORMED WITH A YEDA HOMOLOG TO ENHANCE L-AMINO ACID PRODUCING ACTIVITY, AND METHODS FOR PRODUCING AN L-AMINO ACID USING SAME

(75) Inventors: Vitaliy Arkadyevich Livshits, Moscow (RU); Maria Viacheslavovna Vitushkina, Moscow (RU); Mikhail Markovich Gusyatiner, Moscow (RU); Mikhail Kharisovich Ziyatdinov, Moscow (RU); Valery Zavenovich Akhverdian, Moscow (RU); Ekaterina Alekseevna Savrasova, Moscow (RU); Vera Georgievna Doroshenko, Moscow (RU); Sergey Vladimirovich Mashko, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 340 days.

(21) Appl. No.: 10/302,983

(22) Filed: Nov. 25, 2002

(65) Prior Publication Data

US 2003/0148473 A1    Aug. 7, 2003

(30) Foreign Application Priority Data

Nov. 23, 2001   (RU)   ............................... 2001131570

(51) Int. Cl.
*C12N 1/21* (2006.01)
*C12P 13/04* (2006.01)
*C12P 13/22* (2006.01)
*C12P 13/08* (2006.01)
*C12N 15/00* (2006.01)
*C12P 21/06* (2006.01)
*C07K 14/00* (2006.01)
*C07H 21/04* (2006.01)

(52) U.S. Cl. ................. 435/252.33; 435/106; 435/108; 435/115; 435/252.3; 435/320.1; 435/69.1; 435/440; 536/23.1; 536/23.7; 530/350

(58) Field of Classification Search ........... 435/252.33, 435/320.1, 106, 108, 115, 252.3, 69.1, 440; 536/23.7, 23.1; 530/350
See application file for complete search history.

(56) References Cited

U.S. PATENT DOCUMENTS

| 3,786,039 A | 1/1974 | Ariyoshi et al. ......... 260/112.5 |
| 5,175,107 A | 12/1992 | Debabov et al. |
| 5,534,421 A | 7/1996 | Livshits et al. |
| 5,538,873 A | 7/1996 | Debabov et al. |
| 5,631,157 A | 5/1997 | Debabov et al. |
| 5,658,766 A | 8/1997 | Livshits et al. |
| 5,705,371 A | 1/1998 | Debabov et al. |
| 5,972,663 A | 10/1999 | Winterhalter et al. |
| 5,976,843 A | 11/1999 | Debabov et al. |
| 6,132,999 A | 10/2000 | Debabov et al. |
| 6,165,756 A | 12/2000 | Debabov et al. |
| 6,297,031 B1 | 10/2001 | Debabov et al. |
| 6,303,348 B1 | 10/2001 | Livshits et al. |

FOREIGN PATENT DOCUMENTS

| EP | 0 877 090 | 11/1998 |
| EP | 0 994 190 | 4/2000 |
| EP | 1013765 | * 6/2000 |
| EP | 1 016 710 | 7/2000 |
| RU | 974817 | 8/1990 |
| WO | WO97/23597 | 7/1997 |
| WO | 1 013 765 | 6/2000 |
| WO | WO01/70955 | 9/2001 |

OTHER PUBLICATIONS

Blattner et al., The complete genome sequence of *Escherichia coli* K-12, 1997, Science 277. pp. 1453-1474.*
Lehninger et al., Principles of Biochemistry, 1997, Worth Publishers, Second Edition, pp. 697-715.*
Calton et al., Biotechnology, vol. 4, pp. 317-320, 1986.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Bhagwat et al., J. Bacteriol. 166(3):751-755, 1986.*
Meinkoth and Wahl, Current Protocols in Molecular Biology, Hybridization Analysis of DNA Blots, pp. 2.10.8-2.10.11, 1993.*
T. Dassler, et al., Molecular Microbiology, vol. 36, No. 5, pp. 1101-1112, "Identification of a Major Facilitator Protein From *Escherichia coli* Involved in Efflux of Metabolites of the Cysteine Pathway", 2000.
L. Gold, et al., Ann. Rev. Microbiol., vol. 35, pp. 365-403, "Translational Initiation in Prokaryotes", 1981.
Abstracts of 17th International Congress of Biochemistry and Molecular Biology in conjunction with 1997 Annual Meeting of the American Society for Biochemistry and Molecular Biology, Abstract No. 457, Aug. 24-29, 1997.
A. Hui, et al., The EMBO Journal, vol. 3, No. 3, pp. 623-629, "Mutagenesis of the Three Bases Preceding the Start Codon of the β-Galactosidase mRNA and its Effect on Translation in *Escherichia coli*", 1984.
O. B. Astaurova, et al., Applied Biochemistry and Microbiology, vol. 27. No. 5, pp. 556-561, "Comparative Study of Amino-Acid-Producing E. coli Strains", Sep.-Oct. 1991.
O. B. Astaurova, et al., Applied Biochemistry and Microbiology, vol. 21, No. 5, pp. 485-490, "Animation in Strains of *Escherichia coli* Which Effectively Synthesize Threonine", Sep.-Oct. 1985.
A. Y. Chistoserdov, et al., Plasmid, vol. 16, pp. 161-167, "Broad Host Range Vectors Derived From an RSF1010: : Tn1 Plasmid", 1986.

(Continued)

*Primary Examiner*—Delia M. Ramirez
(74) *Attorney, Agent, or Firm*—Cermak & Kenealy, LLP; Shelly Guest Cermak

(57) ABSTRACT

A method for producing an L-amino acid, such as L-phenylalanine or L-threonine, is provided using a bacterium belonging to the genus *Escherichia*, wherein the L-amino acid productivity of said bacterium is enhanced by enhancing an activity of the protein encoded by the yedA gene.

9 Claims, No Drawings

OTHER PUBLICATIONS

M. M. Gusyatiner, et al., Genetika (Genetics), vol. XIV. No. 6, pp. 957-968, "Investigation of the relA Gene Function in the Expression of Amino Acid Operons", Jun. 1978 (with English translation).

Blattner, F. R., et al., "The Complete Genome Sequence of *Escherichia coli* K-12," Science 1997;277:1453-1462.

Itoh, T., et al., "A 460-kb DNA Sequence of the *Escherichia coli* K-12 Genome Corresponding to the 40.1-50.0 min Region on the Linkage Map," DNA Research 1996;3:379-392.

International Search Report for PCT Appl. No. PCT/JP02/12202 (Mar. 4, 2003).

Zakataeva, N. P., et al., "Characterization of a Pleiotropic Mutation that Confers Upon *Escherichia coli* Cells Resistance to High Concentrations of Homoserine and Threonine," FASEB J. 1997;11(9):A935.

Zakataeva et al., "The novel transmembrane *Escherichia coli* proteins involved in the amino acid efflux", FEBS Letters, 1999, vol. 452, pp. 228-232.

Aleshin et al., "A new family of amino-acid-efflux proteins", TIBS Trends in Biochemical Sciences, 1999, vol. 24, No. 4, pp. 133-135.

European Search Report, Dec. 10, 2004.

U.S. Appl. No. 09/459,573, filed Dec. 13, 1999, Aleoshin, et al.

U.S. Appl. No. 09/466,935, filed Dec. 20, 1999, Livshits, et al.

U.S. Appl. No. 09/761,782, filed Jan. 18, 2001, Livshits, et al.

U.S. Appl. No. 09/841,609, filed Apr. 25, 2001, Livshits, et al.

U.S. Appl. No. 09/847,392, filed May 3, 2001, Livshits, et al.

U.S. Appl. No. 09/903,765, filed Jul. 13, 2001, Debabov, et al.

U.S. Appl. No. 09/927,395, filed Aug. 13, 2001, Livshits, et al.

U.S. Appl. No. 10/302,997, filed Nov. 25, 2002, Vitushkina, et al.

U.S. Appl. No. 10/302,983, filed Nov. 25, 2002, Livshits, et al.

\* cited by examiner

SEQUENCE LISTING

<160> NUMBER OF SEQ ID NOS: 8

<210> SEQ ID NO 1
<211> LENGTH: 921
<212> TYPE: DNA
<213> ORGANISM: Escherichia coli

<400> SEQUENCE: 1

```
atgcgtttcc gccagttgtt accgcttttt ggcgcgctgt ttgcgttgta tatcatttgg     60
ggctcaacct attttgtcat tcggattggc gtggaaagct ggcctccgtt aatgatggcg    120
ggcgttcgat tcctggcagc cggtatttta ttgctggcat ttttgctact gcgcggacac    180
aaactccccc cgctacgtcc gctgctcaat gccgcgctga ttggcctgtt attgctggct    240
gtcggtaatg gcatggtgac ggttgccgaa catcaaaatg ttccttccgg catcgccgcc    300
gtagtggttg caaccgtgcc cctctttacc ctgtgcttca gccgcctgtt tggcattaaa    360
acgcgcaaac tggaatgggt gggtattgcc attgggcttg ccggaatcat catgctcaat    420
agcggtggaa atttaagcgg caatccgtgg ggcgcgattc tgatttttaat cggctcgatt    480 agctgggcgt ttggctcagt ttatggctcg cgcattacct tacctgtagg gatgatggcg    540
ggtgcgattg agatgctggc ggcaggcgtg gtgttaatga tcgcgtcgat gattgcgggt    600
gaaaaactga cggcgctccc ttcccttttca ggcttccttg cggtcggcta tctggcgctg    660
tttggttcga ttatcgccat caacgcttat atgtatttaa tccgtaatgt cagtccggct    720
ctcgccacca gctacgctta cgttaacccg gtggtcgcgg tcttgctggg tacgggactg    780
ggtggagaaa cactgtcgaa gattgaatgg ctggcgctcg gcgtaattgt cttcgcggtg    840
gtactggtca cgttgggaaa atatctcttc ccggcaaaac ccgtagttgc gccagttatt    900
caggacgcat caagcgagta a                                              921
```

<210> SEQ ID NO 2

```
<211> LENGTH: 306
<212> TYPE: PRT
<213> ORGANISM: Escherichia coli

<400> SEQUENCE: 2

Met Arg Phe Arg Gln Leu Leu Pro Leu Phe Gly Ala Leu Phe Ala Leu
1               5                   10                  15

Tyr Ile Ile Trp Gly Ser Thr Tyr Phe Val Ile Arg Ile Gly Val Glu
            20                  25                  30

Ser Trp Pro Pro Leu Met Met Ala Gly Val Arg Phe Leu Ala Ala Gly
        35                  40                  45

Ile Leu Leu Leu Ala Phe Leu Leu Arg Gly His Lys Leu Pro Pro
50                  55                  60

Leu Arg Pro Leu Leu Asn Ala Ala Leu Ile Gly Leu Leu Leu Leu Ala
65                  70                  75                  80

Val Gly Asn Gly Met Val Thr Val Ala Glu His Gln Asn Val Pro Ser
                85                  90                  95

Gly Ile Ala Ala Val Val Ala Thr Val Pro Leu Phe Thr Leu Cys
                100                 105                 110

Phe Ser Arg Leu Phe Gly Ile Lys Thr Arg Lys Leu Glu Trp Val Gly
            115                 120                 125

Ile Ala Ile Gly Leu Ala Gly Ile Ile Met Leu Asn Ser Gly Gly Asn
130                 135                 140

Leu Ser Gly Asn Pro Trp Gly Ala Ile Leu Ile Leu Ile Gly Ser Ile
145                 150                 155                 160

Ser Trp Ala Phe Gly Ser Val Tyr Gly Ser Arg Ile Thr Leu Pro Val
                165                 170                 175

Gly Met Met Ala Gly Ala Ile Glu Met Leu Ala Ala Gly Val Val Leu
            180                 185                 190

Met Ile Ala Ser Met Ile Ala Gly Glu Lys Leu Thr Ala Leu Pro Ser
        195                 200                 205

Leu Ser Gly Phe Leu Ala Val Gly Tyr Leu Ala Leu Phe Gly Ser Ile
    210                 215                 220

Ile Ala Ile Asn Ala Tyr Met Tyr Leu Ile Arg Asn Val Ser Pro Ala
225                 230                 235                 240

Leu Ala Thr Ser Tyr Ala Tyr Val Asn Pro Val Val Ala Val Leu Leu
                245                 250                 255

Gly Thr Gly Leu Gly Gly Glu Thr Leu Ser Lys Ile Glu Trp Leu Ala
            260                 265                 270

Leu Gly Val Ile Val Phe Ala Val Val Leu Val Thr Leu Gly Lys Tyr
        275                 280                 285

Leu Phe Pro Ala Lys Pro Val Val Ala Pro Val Ile Gln Asp Ala Ser
    290                 295                 300

Ser Glu
305

<210> SEQ ID NO 3
<211> LENGTH: 25
<212> TYPE: DNA
<213> ORGANISM: Artificial Sequence
<220> FEATURE:
<223> OTHER INFORMATION: synthetic DNA

<400> SEQUENCE: 3
aagggatccc tctcattttt attgt                                         25
```

-continued

```
<210> SEQ ID NO 4
<211> LENGTH: 23
<212> TYPE: DNA
<213> ORGANISM: Artificial Sequence
<220> FEATURE:
<223> OTHER INFORMATION: synthetic DNA

<400> SEQUENCE: 4
aagcgtcgac cgagcgtctg gaa                                          23

<210> SEQ ID NO 5
<211> LENGTH: 29
<212> TYPE: DNA
<213> ORGANISM: Artificial Sequence
<220> FEATURE:
<223> OTHER INFORMATION: synthetic DNA

<400> SEQUENCE: 5
gaccatagat ctgaattcga gctcggtac                                    29

<210> SEQ ID NO 6
<211> LENGTH: 29
<212> TYPE: DNA
<213> ORGANISM: Artificial Sequence
<220> FEATURE:
<223> OTHER INFORMATION: synthetic DNA

<400> SEQUENCE: 6
acggccagat ctaagcttgc atgcctgca                                    29

<210> SEQ ID NO 7
<211> LENGTH: 34
<212> TYPE: DNA
<213> ORGANISM: Artificial Sequence
<220> FEATURE:
<223> OTHER INFORMATION: synthetic DNA

<400> SEQUENCE: 7
aacagtgatc atttgcctgg cggcagtagc gcgg                              34

<210> SEQ ID NO 8
<211> LENGTH: 41
<212> TYPE: DNA
<213> ORGANISM: Artificial Sequence
<220> FEATURE:
<223> OTHER INFORMATION: synthetic DNA

<400> SEQUENCE: 8
ataaaaagct tagatctcaa aaagagtttg tagaaacgca a                      41
```

US 7,259,003 B2

ESCHERICHIA BACTERIA TRANSFORMED WITH A YEDA HOMOLOG TO ENHANCE L-AMINO ACID PRODUCING ACTIVITY, AND METHODS FOR PRODUCING AN L-AMINO ACID USING SAME

TECHNICAL FIELD

The present invention relates to biotechnology, specifically to a method for producing L-amino acids by fermentation and more specifically to a gene derived from bacterium *Escherichia Coli*. The gene is useful for improvement of L-amino acid productivity, for example, L-phenylalanine and L-threonine.

BACKGROUND ART

Conventionally the L-amino acids have been industrially produced by method of fermentation utilizing strains of microorganisms obtained from natural sources or mutants of the same especially modified to enhance L-amino acid productivity.

There have been disclosed many techniques to enhance L-amino acid productivity, for example, by transformation of microorganism by recombinant DNA (see, for example, U.S. Pat. No. 4,278,765). These techniques is based on increasing of activities of the enzymes involved in amino acid biosynthesis and/or desensitizing the target enzymes from the feedback inhibition by produced L-amino acid (see, for example, Japanese Laid-open application No56-18596 (1981), WO 95/16042 or U.S. Pat. Nos. 5,661,012 and 6,040,160).

On the other hand, the enhancement of amino acid excretion activity may improve the productivity of L-amino acid producing strain. Lysine-producing strain of a bacterium belonging to the genus *Corynebacterium* having increased expression of L-lysine excretion gene (lysE gene) is disclosed (WO 9723597A2). In addition, genes encoding efflux proteins suitable for secretion of L-cysteine, L-cystine, N-acetylserine or thiazolidine derivatives are also disclosed (U.S. Pat. No. 5,972,663).

At present, several *Escherichia coli* genes encoding putative membrane proteins enhancing L-amino acid production are disclosed. Additional copies of rhtB gene make a bacterium more resistant to L-homoserine and enhance the production of L-homoserine, L-threonine, L-alanine, L-valine and L-isoleucine (European patent application EP994190A2). Additional copies of the rhtC gene make a bacterium more resistant to L-homoserine and L-threonine and enhance production of L-homoserine, L-threonine and L-leucine (European patent application EP1013765A1). Additional copies of yahN, yeaS, yfiK and yggA genes enhance production of L-glutamic acid, L-lysine, L-threonine, L-alanine, L-histidine, L-proline, L-arginine, L-valine and L-isoleucine (European patent application EP1016710A2).

Earlier the present inventors obtained, with respect to *E. coli* K-12, a mutant having a mutation, thrR (herein referred to as rhtA23) that is concerned in resistance to high concenrations of threonine or homoserine in a minimal medium (Astaurova, O. B. et al., Appl. Biochem. Microbiol., 21, 611-616, 1985). The mutation improved the production of L-threonine (SU Patent No. 974817), homoserine and glutamate (Astaurova, O. B. et al., Appl. Biochem. Microbiol., 27, 556-561, 1991) by the respective *E. coli* producing strains.

Furthermore, the present inventors have revealed that the rhtA gene exists at 18 min on *E. coli* chromosome close to the glnHPQ operon that encodes components of the glutamine transport system, and that the rhtA gene is identical to ybiF ORF between pexB and ompX genes. The unit expressing a protein encoded by the ORF has been designated as rhtA (rht: resistance to homoserine and threonine) gene.

Besides, the present inventors have found that the rhtA gene amplification also conferred resistance to homoserine and threonine. The rhtA23 mutation is an A-for-G substitution at position −1 with respect to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457). It is known that a nucleotide composition of the spacer between the SD sequence and start codon and especially the sequences immediately upstream of the start codon profoundly affect mRNA translatability. A 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Therefore, it may be suggested that rhtA23 mutation increases rhtA gene expression.

The rhtA gene encodes a protein that consists of 295 amino acid residues and is a highly hydrophobic protein containing 10 predicted transmembrane segments. A PSI-BLAST search of the nucleotide sequence of *E. coli* strain K-12 belonging to the genus *Escherichia* (Science, 277, 1453-1474 (1997) revealed at least 10 proteins homologous to RhtA. Among them there are proteins encoded by ydeD and yedA genes. Earlier it was shown the ydeD gene is involved inefflux of the cysteine pathway metabolites (Daβler et al., Mol. Microbiol., 36, 1101-1112, 2000; U.S. Pat. No. 5,972,663). The yedA gene has been known as putative transmembrane subunit, which may encode functionally unknown protein (numbers 8037 to 8957 in the sequence of GenBank accession AE000287 U00096).

DISCLOSURE OF THE INVENTION

An object of present invention is to enhance the productivity of L-amino acid producing strains and to provide a method for producing L-amino acid, for example, L-phenylalanine and L-threonine using these strains.

This aim was achieved by identifying that the yedA gene encoding a membrane protein, homologue to RhtA, which is not involved in biosynthetic pathway of a target L-amino acid, conferred a microorganism resistance to several amino acids and amino acid analogues when the wild type allele of the gene was amplified on a multicopy vector in the microorganism. Besides, yedA gene can enhance amino acid production when its additional copies are introduced into the cells of the respective producing strain. Thus the present invention has been completed.

The present inventions are as follows:

1) An L-amino acid producing bacterium belonging to the genus *Escherichia*, wherein the L-amino acid production by the bacterium is enhanced by enhancing an activity of a protein as defined in the following (A) or (B) in a cell of the bacterium:

(A) a protein which comprises the amino acid sequence shown in SEQ ID NO:2 in Sequence listing;

(B) a protein which comprises an amino acid sequence including deletion, substitution, insertion or addition of one or several amino acids in the amino acid sequence shown in SEQ ID NO:2 in Sequence listing, and which has an activity of making the bacterium having enhanced resistance to an L-amino acid, such as phenylalanine, threonine, homoserine, or cysteine and/or an amino acid analog such as p-fluoro-phenylalanine, 5-fluoro-DL-tryptophane, S-(2-aminoethyl)cysteine, or 4-aza-DL-leucine;

(hereinafter, the proteins as defined in the above (A) or (B) are referred to as "proteins of the present invention")

2) The bacterium according to the above bacterium, wherein the activity of the protein as defined in (A) or (B) is enhanced by transformation of the bacterium with a DNA coding for the proteins as defined in (A) or (B), or by alteration of expression regulation sequence of said DNA on the chromosome of the bacterium.

3) The bacterium according to the above bacterium, wherein the transformation is performed with a multi-copy vector containing the DNA.

4) A method for producing an L-amino acid, which comprises cultivating the bacterium according to the above bacterium in a culture medium and collecting from the culture medium the L-amino acid to be produced and accumulated in the medium.

5) The method according to the above method, wherein the L-amino acid to be produced is L-phenylalanine.

6) The method according to the above method, wherein the bacterium has enhanced expression of genes for phenylalanine biosynthesis.

7) The method according to the above method, wherein the L-amino acid to be produced is L-threonine.

8) The method according to the above method, wherein the bacterium has enhanced expression of threonine operon.

9) A method for producing lower alkyl ester of α-L-aspartyl-L-phenylalanine, comprising
cultivating the bacterium according the above acterium in a culture medium to produce and accumulate L-phenylalanine in the medium, said bacterium having L-phenylalanine productivity, and
synthesizing lower alkyl ester of α-L-aspartyl-L-phenylalanine from aspartic acid or its derivative and the obtained L-phenylalanine.

10) The method according to the above method, further comprising
esterifying L-phenylalanine to generate a lower alkyl ester of L-phenylalanine,
condensing the lower alkyl ester of L-phenylalanine with the aspartic acid derivative, wherein the derivative is N-acyl-L-aspartic anhydride,
separating the lower alkyl ester of N-acyl-α-L-aspartyl-L-pheflylalaflifle from the reaction mixture, and
hydrogenating the lower alkyl ester of N-acyl-α-L-aspartyl-L-phenylalanifle to generate the lower alkyl ester of α-L-aspartyl-L-phenylalanine.In the present invention, an amino acid is of L-configuration unless otherwise noted.

The method for producing L-amino acid includes production of L-phenylalanine using L-phenylalanine producing bacterium wherein activities of the proteins of the present invention such as that comprising amino acid sequence shown in SEQ ID NO:2 are enhanced. Also, method for producing L-amino acid includes production L-threonine using L-threonine producing bacterium wherein activities of the proteins of the present invention such as that comprising amino acid sequence shown in SEQ ID NO:2 are enhanced.

The present invention will be explained in detail below.

The bacterium of the present invention is an L-amino acid producing bacterium belonging to the genus *Escherichia*, wherein L-amino acid production by the bacterium is enhanced by enhancing an activity of the proteins of the present invention in a cell of the bacterium.

In the present invention, "L-amino acid producing bacterium" means a bacterium which has an ability to produce and accumulate the L-amino acid in a medium, when the bacterium is cultured in the medium. The L-amino acid producing ability may be possessed by the bacterium as a property of a wild strain of the bacterium or may be imparted or enhanced by breeding.

A bacterium of present invention is L-amino acid producing bacterium belonging to the genus *Escherichia* having enhanced activities of proteins, which enhance the productivity of the target L-amino acid. Concretely the bacterium of the present invention is L-amino acid producing bacterium belonging to the genus *Escherichia* that has enhanced activities of the proteins of the present invention. More concretely, the bacterium of the present invention harbors the DNA having yedA gene overexpressed in the chromosome or in a plasmid in the bacterium and has enhanced ability to produce L-amino acid, for example, L-phenylalanine and L-threonine using these strains.

The protein of the present invention includes those as defined in the following, (A) or (B):
(A) a protein which comprises the amino acid sequence shown in SEQ ID NO:2 in Sequence listing;
(B) a protein which comprises an amino acid sequence including deletion, substitution, insertion or addition of one or several amino acids in the amino acid sequence shown in SEQ ID NO:2 in Sequence listing, and which has an activity of making bacterium having enhanced resistance to an L-amino acid such as phenylalanine, threonine, homoserine, or cysteine and/or an amino acid analogs such as p-fluoro-phenylalanine, 5 -fluoro-DL-tryptophan, S-(2-aminoethyi)cysteine-, or 4-aza-DL-leucine.

The number of "several" amino acids differs depending on the position or the type of amino acid residues in the three-dimensional structure of the protein. It may be 2 to 30, preferably 2 to 15, and more preferably 2 to 5 for the protein (A).

"Resistance to an L-amino acid and/or an amino acid analog" means ability for bacterium to grow on a minimal medium containing L-amino acid or its analog in concentration under which unmodified or the wild type, or the parental strain of the bacterium cannot grow, or ability for bacterium to grow faster on a medium containing L-amino acid or amino acid analog than unmodified or the wild type, or the parental strain of the bacterium. L-amino acid analogs are exemplified by p-fluoro-phenylalanine, 5-fluoro-DL-tryptophane, S-(2-aminoethyl)cysteine, 4-aza-DL-leucine or the like. Above mentioned concentration of L-amino acid or amino acid analog is generally 1000 to 10000 μg/ml, preferably 3000 to 5000 μg/ml in case of L-homoserine, preferably 5000 to 7000 μg/ml in case of serine and cysteine, generally 0.1 to 1.0 μg/ml, preferably 0.2 to 0.5 μg/ml in case of 5-fluoro-DL-tryptophane, generally 0.1 to 2.0 mg/ml, preferably 0.5 to 1.0 mg/ml in case of p-fluoro-phenylalanine; generally 0.1 to 2.0 mg/ml, preferably 0.5 to 1.0 mg/ml in case of 4-aza-DL-leucine and S-(2-aminoethyl)cysteine.

The bacterium of the present invention also includes one wherein the activity of the proteins of the present invention is enhanced by transformation of said bacterium with DNA coding for the protein as defined in (A) or (B), or by alteration of expression regulation sequence of said DNA on the chromosome of the bacterium.

The DNA, which is used for modification of the bacterium of the present invention may code for a protein having L-amino acid excretion activity. More concretely, the DNA is represented by yedA gene. The yedA gene can be obtained by, for example, PCR using primers based on the nucleotide sequence shown-in SEQ ID No: 1.

The DNA of the present invention includes a DNA coding for the protein which include deletion, substitution, insertion or addition of one or several amino acids in one or more positions on the protein (A) as long as they do not lose the activity of the protein. Although the number of "several" amino acids differs depending on the position or the type of amino acid residues in the three-dimensional structure of the protein, it may be 2 to 30, preferably 2 to 15, and more preferably 2 to 5 for the protein (A). The DNA coding for substantially the same protein as the protein defined in (A) may be obtained by, for example, modification of nucleotide sequence coding for the protein defined in (A) using site-directed mutagenesis so that one or more amino acid residue will be deleted, substituted, inserted or added. Such modified DNA can be obtained by conventional methods using treatment with reagents and conditions generating mutations. Such treatment includes treatment the DNA coding for proteins of present invention with hydroxylamin or treatment the bacterium harboring the DNA with UV irradiation or reagent such as N-methyl-N'-nitro-N-nitrosoguanidine or nitrous acid.

The DNA of the present invention includes variants which can be found in the different strains and variants of bacteria belonging to the genus *Escherichia* according to natural diversity. The DNA coding for such variants can be obtained by isolating the DNA, which hybridizes with yedA gene or part of the gene under the stringent conditions, and which codes the protein enhancing L-amino acid production. The term "stringent conditions" referred to herein as a condition under which so-called specific hybrid is formed, and non-specific hybrid is not formed. For example, the stringent conditions includes a condition under which DNAs having high homology, for instance DNAs having homology no less than 70% to each other, are hybridized. Alternatively, the stringent conditions are exemplified by conditions which comprise ordinary condition of washing in Southern hybridization, e.g., 60° C., 1×SSC, 0.1% SDS, preferably 0.1× SSC, 0.1% SDS. As a probe for the DNA that codes for variants and hybridizes with yedA gene, a partial sequence of the nucleotide sequence of SEQ ID NO: 1 can also be used. Such a probe may be prepared by PCR using oligo-nucleotides produced based on the nucleotide sequence of SEQ ID NO: 1 as primers, and a DNA fragment containing the nucleotide sequence of SEQ ID NO: 1 as a template. When a DNA fragment in a length of about 300 bp is used as the probe, the conditions of washing for the hybridization consist of, for example, 50° C., 2×SSC, and 0.1% SDS.

Transformation of bacterium with a DNA coding for a protein means introduction of the DNA into bacterium cell for example by conventional methods to increase expression of the gene coding for the protein of the present invention and to enhance the activity of the protein in the bacterial cell.

The methods of the enhancement of gene expression include an increasing of the gene copy number. Introduction of a gene into a vector that is able to function in a bacterium belonging to the genus *Escherichia* increases copy number of the gene. For such purposes multi-copy vectors can be preferably used. The multi-copy vector is exemplified by pBR322, pUC19, pBluescript KS⁺, pACYC177, pACYC184, pAYC32, pMW119, pET22b or the like.

Besides, enhancement of gene expression can be achieved by introduction of multiple copies of the gene into bacterial chromosome by, for example, method of homologous recombination or the like.

In case that expression of two or more genes is enhanced, the genes may be harbored together on the same plasmid or separately on different plasmids. It is also acceptable that one of the genes is harbored on a chromosome, and the other gene is harbored on a plasmid.

On the other hand, the enhancement of gene expression can be achieved by locating the DNA of the present invention under control of a potent promoter instead of the native promoter. Strength of promoter is defined by frequency of acts of the RNA synthesis initiation. Methods for evaluation the strength of promoter and an examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, $P_L$ promoter of lambda phage are known as potent constitutive promoter. Other known potent promoters are lac promoter, trp promoter, trc promoter, and the like. Using the potent promoter can be combined with multiplication of gene copies.

Methods for preparation of chromosomal DNA, hybridization, PCR, preparation of plasmid DNA, digestion and ligation of DNA, transformation, selection of an oligonucleotide as a primer and the like may be ordinary methods well known to one skilled in the art. These methods are described in Sambrook, J., Fritsch, E. F., and Maniatis, T., "Molecular Cloning A Laboratory Manual, Third Edition", Cold Spring Harbor Laboratory Press (2001) and the like.

The bacterium of the present invention can be obtained by introduction of the aforementioned DNAs into bacterium belonging to the genus *Escherichia* inherently having ability to produce L-amino acid. Alternatively, the bacterium of present invention can be obtained by imparting ability to produce L-amino acid to the bacterium belonging to the genus *Escherichia* already harboring the DNAs.

A bacterium belonging to the genus *Escherichia* is not particularly limited so long as it has an ability to produce L-amino acid or it can be conferred the ability. The examples of the bacterium belonging to the genus *Escherichia* include *Escherichia coli*. Examples of amino acid-producing bacteria belonging to the genus *Escherichia* are described below.

Phenylalanine Producing Bacteria

As a parent strain which is to be enhanced in activity of the protein of the present invention, the phenylalanine-producing bacterium strains belonging to the genus *Escherichia*, such as strain AJ12739 (tyrA::Tn10, tyrR) (VKPM B-8197); strain HW1089 (ATCC Accession No. 55371) harboring pheA34 gene (U.S. Pat. No. 5,354,672); mutant MWEC101-b strain (KR8903681); strains NRRL B-12141, NRRL B-12145, NRRL B-12146 and NRRL B-12147 (U.S. Pat. No. 4,407,952) and the like may be used. Also as a parent strain which is to be enhanced in activity of the protein of the present invention, the phenylalanine-producing bacterium belonging to the genus *Eschserichia*, the *E. coli* strain K-12 [W3110 (tyrA)/pPHAB (FERM BP-3566), *E. coli* strain K-12 [W3110 (tyrA)/pPHAD] (FERM BP-12659), *E. coli* K-12 [W3110 (tyrA)/pPHATerm] (FERM BP-12662) and *E. coli* strain K-12 [W3110 (tyrA)/pBR-aroG4, pACMAB] named as AJ 12604 (FERM BP-3579) may be used (European patent EP488424B1).

Threonine Producing Bacteria

As a parent strain which is to be enhanced in activity of the protein of the present invention, the threonine producing bacterium strains belonging to the genus *Eschserichia*, such as strain MG442 (VKPM B-1628) (Gusyatiner, et al., Genetika (in Russian), 14, 947-956, 1978, (U.S. Pat. No. 4,278, 765); VKPM B-3996 (U.S. Pat. No. 6,165,756); VKPM B-5318 (U.S. Pat. No. 6,132,999); BP-3756 and BP-4072 (U.S. Pat. No. 5,5,474,918); FERM BP-3519 and FERM BP-3520 (U.S. Pat. No. 5,376,538) and the like may be used.

The method of the present invention includes method for producing an L-amino acid, comprising steps of cultivating the bacterium of the present invention in a culture medium, to allow the L-amino acid to be produced and accumulated in the culture medium, and collecting the L-amino acid from the culture medium. Also, the method of the present invention includes method for producing L-phenylalanine, comprising steps of cultivating the bacterium of the present invention in a culture medium, to allow L-phenylalanine to be produced and accumulated in the culture medium, and collecting L-phenylalanine from the culture medium. Also, the method of the present invention includes method for producing L-threonine, comprising steps of cultivating the bacterium of the present invention in a culture medium, to allow L-threonine to be produced and accumulated in the culture medium, and collecting L-threonine from the culture medium.

In the present invention, the cultivation, the collection and purification of L-amino acid from the medium and the like may be performed in a manner similar to the conventional fermentation method wherein an amino acid is produced using a microorganism. A medium used for culture may be either a synthetic medium or a natural medium, so long as the medium includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the used microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium chloride, and the like are used. Some additional nutrient can be added to the medium if necessary. For instance, if the microorganism requires tyrosine for growth (tyrosine auxotrophy) the sufficient amount of tyrosine can be added to the medium for cultivation.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by conventional method such as ion-exchange, concentration and crystallization methods.

Phenylalanine produced by the method of the present invention may be used for, for example, producing lower alkyl ester of α-L-aspartyl-L-phenylalanine (also referred to as "aspartame"). That is, the method of the present invention includes method for producing lower alkyl ester of α-L-aspartyl-L-phenylalanine by using L-phenylalanine as a raw material. The method comprising synthesizing lower alkyl ester of α-L-aspartyl-L-phenylalanine from L-phenylalanine produced by the method of the present invention as described above and aspartic acid or its derivative. As lower alkyl ester, methyl ester, ethyl ester and propyl ester, or the like can be mentioned.

In the method of the present invention, a process for synthesizing lower alkyl ester of α-L-aspartyl-L-phenylalanine from L-phenylalanine and aspartic acid or its derivative is not particularly limited and any conventional method can be applied so long as L-phenylalanine or its derivative can be used for synthesis of lower alkyl ester of α-L-aspartyl-L-phenylalanine. Concretely, for example, lower alkyl ester of α-L-aspartyl-L-phenylalanine may be produced by the following process (U.S. Pat. No. 3,786,039). L-phenylalanine is esterified to obtain lower alkyl ester of L-phenylalanine. The L-phenylalanine alkyl ester is reacted with L-aspartic acid derivative of which amino group and β-carboxyl group are protected and α-carboxyl group is esterified to activate. The derivative includes N-acyl-L-aspartic anhydride such as N-formyl-, N-carbobenzoxy-, or N-p-methoxycarbobenzoxy-L-aspartic anhydride. By the condensation reaction, mixture of N-acyl-α-L-aspartyl-L-phenylalanine and N-acyl-β-L-aspartyl-L-phenylalanine is obtained. If the condensation reaction is performed under existence of an organic acid of which acid dissociation constant at 37° C. is 10-4 or less, ratio of α form to β form in the mixture is increased (Japanese Patent Laid-Open Publication No. 51-113841). Then the N-acyl-α-L-aspartyl-L-phenylalanine is separated from the mixture, followed by hydrogenating to obtain α-L-aspartyl-L-phenylalanine.

BEST MODE FOR CARRYING OUT THE INVENTION

The present invention will be more concretely explained below with reference to Examples.

EXAMPLE 1

Cloning the yedA Gene from *E. coli*

The entire nucleotide sequence of *E. coli* strain K-12 has already been determined (Science, 277, 1453-1474, 1997). A PSI-BLAST search revealed that at least 10 rhtA paralogues including yedA gene are present in the genome of *E. coli* K-12. The yedA gene encodes putative transmembrane subunit function of which is unknown.

Based on the reported nucleotide sequence the primers depicted in SEQ ID No. 3 (primer 1) and No. 4 (primer 2) were synthesized. The primer 1 is a sequence complementary to a sequence from 179 to 153 nucleotides upstream start codon with a restriction enzyme BamHI recognition site introduced at the. 5'-end thereof. The primer 2 is a sequence complementary to a sequence from 53 to 77 nucleotides downstream stop codon with a restriction enzyme SalI recognition site introduced at the 5'-end thereof.

The chromosomal DNA of *E. coli* TG1 strain was prepared by an ordinary method. PCR was carried out on "Perkin Elmer GeneAmp PCR System 2400" under the following conditions: 40 sec. at 95° C., 40 sec. at 47° C., 40 sec. at 72° C., 30 cycles by means of Taq polymerase (Fermentas). The obtained FOR fragment containing yedA gene with its own promoter was treated with BamHI and SalI restrictases and inserted into multicopy vectors pUC 19 or pAYCTER3 previously treated with the same enzymes. Thus, the plasmids pYEDA1 and pYEDA2, respectively, were obtained. The pAYCTER3 vector is a derivative of a pAYC32, a moderate copy number and very stable vector constructed on the basis of plasmid RSF1010 (Christoserdov A. Y., Tsygankov Y. D., Broad-host range vectors derived from a RSF 1010 Tnl plasmid, Plasmid, 1986, v. 16, pp. 161-167). The pAYCTER3 vector was obtained by introduction of the polylinker from pUC19 plasmid and the strong terminator rrnB into the pAYC32 plasmid instead of its promoter as follows. At first, the polylinker from pUG 19 plasmid was obtained by PCR using the primers depicted in SEQ ID No. 5 and No. 6. The obtained PCR product was treated with EcoRI and BglI restrictases. The terminator rrnB also was obtained by PCR using the primers depicted in SEQ ID No. 7 and No. 8. The obtained PCR product was treated with BglII and BclII restrictases. Then, these two DNA fragments were ligated into pAYC32 plasmid previously treated with EcoRI and BelI restrictases. Thus the pAYCTER3 plasmid was obtained.

EXAMPLE 2

The Effect of the yedA Gene Amplification on the Resistance of *E. coli* Strain TG1 to Amino Acids and Amino Acid Analogs The pYEDA1 and pYEDA2 plasmids and the pUC19 and pAYCTER3 vectors were introduced into *E. coli* strain TG1. Thus the strains TG1 (pYEDA1), TG1 (pYEDA2), TG1 (pUC19) and TG1 (pAYCTER3) were obtained.

Then the ability of these strains to grow in the presence of amino acids and amino acid analogues for each strain were determined on M9 glucose minimal agar plates containing graded concentrations of inhibitor. The plates were spotted with $10^6$ to $10^7$ cells from an overnight culture grown in a minimal medium (supplemented with 100 μg/ml of ampicillin for plasmid strains). The growth was estimated after 44 h incubation at 37° C. The results are presented in Table 1.

TABLE 1

| | | Growth after 44 h | | |
|---|---|---|---|---|
| Substrate | Concentration mg/ml | TG1 (pUC19)* | TG1 (pYEDA1) | TG1 (pYEDA2) |
| — | – | + | + | + |
| L-phenylalanine | 20.0 | – | + | – |
| L-homoserine | 3.0 | – | + | n.d. |
| L-threonine | 50.0 | – | + | n.d. |
| L-cysteine | 7.5 | – | + | n.d. |
| L-histidine | 20.0 | – | + | n.d. |
| p-fluoro-DL-phenylalanine | 1.0 | – | + | + |
| p-fluoro-DL-phenylalanine | 2.0 | – | + | – |
| 5-fluoro-DL-tryptophane | 0.0005 | – | + | n.d. |
| S(2-aminoethyl)-L-cysteine | 0.4 | – | + | + |
| 4-aza-DL-leucine | 1.0 | – | + | n.d. |

*The same results were obtained for the TG1 strain harboring pAYCTER3 vector.
+: good growth;
–: no growth;
n.d.—not determined.

EXAMPLE 3

Effect of the yedA Gene Amplification on Phenylalanine Production

The phenylalanine-producing *E. coli* strain AJ12739 was used as a parental strain for transformation with plasmids harboring the yedA gene. The strain AJ12739 has been deposited in the Russian National Collection of Industrial Microorganisms (VKPM) (Russia, 113545 Moscow, 1$^{st}$ Dorozhny proezd, 1) on Nov. 6, 2001 under accession number VKPM B-8197. The original deposit was converted to international deposit according to Budapest Treaty on Aug. 23, 2002.

The phenylalanine-producing strain AJ12739 was transformed with the pYEDA2 plasmid or with the pAYCTER3 vector to obtain the AJ12739/pYEDA2 and AJ12739/pAYCTER3 strains. These strains were each cultivated at 37° C. for 18 hours in a nutrient broth with 100 mg/l ampicillin, and 0.3 ml of the obtained culture was inoculated into 3 ml of a fermentation medium containing 100 mg/l ampicilline, in a 20×200 mm test tube, and cultivated at 37° C. for 48 hours with a rotary shaker. After the cultivation, an accumulated amount of phenylalanine in the medium was determined by TLC. 10×15 cm TLC plates coated with 0.11 mm layers of Sorbfil silica gel without fluorescent indicator (Stock Company Sorbpolymer, Krasnodar, Russia) were used. Sorbfil plates were developed with a mobile phase: propan-2-ol:ethylacetate:25% aqueous ammonia water=40:40:7:16 (v/v). A solution (2%) of ninhydrin in acetone was used as a visualizing reagent. The results are presented in Table 2.

The composition of the fermentation medium (g/l):

| | |
|---|---|
| Glucose | 40.0 |
| $(NH_4)_2SO_4$ | 16.0 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine- HCl | 0.0002 |
| Yeast extract | 2.0 |
| Tyrosine | 0.1 |
| $CaCO_3$ | 30.0 |

Glucose and magnesium sulfate are sterilized separately. $CaCO_3$ dry-heat are sterilized at 180° for 2 h. pH is adjusted to 7.0. Antibiotic is introduced into the medium after sterilization.

TABLE 2

| *E. coli* strain | $OD_{600}$ | Phenylalanine, g/l |
|---|---|---|
| AJ12739 (pAYCTER3) | 7.0 | 1.5 |
| AJ12739 (pAYCTER-YEDA2) | 7.5 | 1.8 |

It can be seen from the Table 2 that the yedA gene amplification improved phenylalanine productivity of the AJ12739 strain.

EXAMPLE 4

Effect of the yedA Gene Amplification on Threonine Production

The known threonine-producing *E. coli* strain VNIIGenetika MG442 (Gusyatiner, et al., 1978, Genetika (in Russian), 14, p. 947-956) (deposited in the Russian National Collection of Industrial Microorganisms (VKPM) according to Budapest Treaty under accession number VKPM B-1628) was transformed with the pYEDA1 plasmid or with the pUC19 vector resulting the strains MG442/pYEDA1 and MG442/pUC19.

These strains were each cultivated at 37° C. for 18 hours in a nutrient broth with 100 mg/l ampicillin, and 0.3 ml of the obtained culture was inoculate into 3 ml of a fermentation medium containing 100 mg/l ampicilline, in a 20×200 mm test tube, and cultivated at 37° C. for 48 hours with a rotary shaker. After the cultivation, an accumulated amount of threonine in the medium was determined by TLC. Sorbfil plates were developed with a mobile phase:propan-2-ol: acetone:water:25% aqueous ammonia=25:25:7:6 (v/v). A solution (2%) of ninhydrin in acetone was used as a visualizing reagent. The results are presented in Table 3.

The composition of the fermentation medium (g/l):

| | |
|---|---|
| Glucose | 50.0 |
| $(NH_4)_2SO_4$ | 10.0 |
| $K_2HPO_4$ | 1.0 |
| $MgSO_4 \cdot 7H_2O$ | 0.4 |

-continued

| | |
|---|---|
| $FeSO_4 \cdot 7H_2O$ | 0.02 |
| $MnSO_4 \cdot 5H_2O$ | 0.02 |
| Thiamine- HCl | 0.0002 |
| Yeast extract | 1.0 |
| $CaCO_3$ | 20.0 |

Glucose and magnesium sulfate are sterilized separately. $CaCO_3$ dry-heat are sterilized at 180° for 2 h. pH is adjusted to 7.0. Antibiotic is introduced into the medium after sterilization.

TABLE 3

| E. coli strain | Threonine, g/l | Yield, (%) |
|---|---|---|
| MG442 (pUC19) | 2.9 | 5.8 |
| MG442 (pYEDA1) | 4.0 | 8.0 |

It can be seen from the Table 2 that the yedA gene amplification improved threonine productivity of the MG442 strain.

What is claimed is:

1. An *Escherichia coli* bacterium which has an ability to produce and accumulate an L-amino acid selected from the group consisting of L-threonine and L-phenylalanine in a medium, when the bacterium is cultured in the medium, wherein said bacterium has been modified so that the L-amino acid production by said bacterium is enhanced as compared to an unmodified bacterium by enhancing the expression of a DNA that encodes the protein comprising the amino acid sequence shown in SEQ ID NO:2, wherein said expression is enhanced by a method selected from the group consisting of increasing the copy number of said DNA in said bacterium, locating said DNA under the control of a potent promoter instead of the native promoter on the chromosome of the bacterium, and a combination thereof.

2. The bacterium according to claim 1, wherein said DNA is present on a muiticopy vector.

3. An *Escherichia coli* bacterium which has an ability to produce and accumulate an L-amino acid selected from the group consisting of L-threonine and L-phenylalanine in a medium when the bacterium is cultured in the medium, wherein said bacterium has been modified so that the L-amino acid production by said bacterium is enhanced as compared to an unmodified bacterium by enhancing the expression of a DNA that encodes a protein which is encoded by a DNA selected from the group consisting of a) a DNA comprising the nucleotide sequence shown in SEQ ID NO:1, and
b) a DNA encoding a protein comprising the amino acid sequence of SEQ ID NO: 2, except that the sequence may include deletions, substitutions, insertions, or additions of 1 to 5 amino acids, and wherein said protein has an activity of imparting upon a bacterium resistance to an L-amino acid selected from the group consisting of L-phenylalanine, L-threonine, L-homoserine, L-cysteine and L-histidine, and/or imparting upon a bacterium resistance to an amino acid analog selected from the group consisting of p-fluoro-phenylalanine, 5-fluoro-DL-tryptophan, S-(2-aminoethyl) cysteine, and 4-aza-DL-leucine, wherein said expression is enhanced by a method selected from the group consisting of increasing the copy number of said DNA in said bacterium, locating said DNA under the control of a potent promoter instead of the native promoter on the chromosome of the bacterium, and a combination thereof.

4. The bacterium of claim 3, wherein said DNA is present on a multicopy vector.

5. A method for producing an L-amino acid, which comprises cultivating the bacterium according to any of claims 1, 2, 3, or 4 in a culture medium and collecting the L-amino acid from the culture medium.

6. The method according to claim 5, wherein the L-amino acid is L-phenylalanine.

7. The method according to claim 6, wherein the bacterium has increased expression of the genes for phenylalanine biosynthesis.

8. The method according to claim 5, wherein the L-amino acid is L-threonine.

9. The method according to claim 8, wherein the bacterium has increased expression of threonine operon.

* * * * *